(12) United States Patent
Feng et al.

(10) Patent No.: US 9,717,523 B2
(45) Date of Patent: Aug. 1, 2017

(54) PERICARDIOCENTESIS NEEDLE COMPONENT

(75) Inventors: Ji Feng, Beijing (CN); Jie Gong, Beijing (CN); Xin Hua, Beijing (CN); Sophia Wang Hansen, Beijing (CN)

(73) Assignee: SYNAPTIC MEDICAL (BEIJING) CO. LTD., Beijing (CN)

( * ) Notice: Subject to any disclaimer, the term of this patent is extended or adjusted under 35 U.S.C. 154(b) by 237 days.

(21) Appl. No.: 14/123,014

(22) PCT Filed: May 25, 2012

(86) PCT No.: PCT/CN2012/000728
§ 371 (c)(1),
(2), (4) Date: Nov. 27, 2013

(87) PCT Pub. No.: WO2012/163083
PCT Pub. Date: Dec. 6, 2012

(65) Prior Publication Data
US 2014/0094836 A1 Apr. 3, 2014

(30) Foreign Application Priority Data

May 27, 2011 (CN) .......................... 2011 1 0139534

(51) Int. Cl.
*A61B 17/34* (2006.01)
*A61B 17/00* (2006.01)
*A61B 17/22* (2006.01)
*A61M 25/09* (2006.01)

(52) U.S. Cl.
CPC ...... *A61B 17/3478* (2013.01); *A61B 17/3403* (2013.01); *A61B 2017/00247* (2013.01);
(Continued)

(58) Field of Classification Search
CPC ............ A61B 17/3478; A61B 17/3417; A61B 17/6478; A61B 17/3403;
(Continued)

(56) References Cited

U.S. PATENT DOCUMENTS 4,991,578 A 2/1991 Cohen
7,056,314 B1 * 6/2006 Florio ............... A61M 25/0136
604/528
(Continued)

FOREIGN PATENT DOCUMENTS

CN 2574609 Y 9/2003
CN 2621615 Y 6/2004
(Continued)

OTHER PUBLICATIONS

Telreja et al. Clinical Investigation and Reports. Sep. 2003. American Heart Association. 108:1852-1857.*

*Primary Examiner* — Eric Rosen
*Assistant Examiner* — Mikail Mannan
(74) *Attorney, Agent, or Firm* — Pillsbury Winthrop Shaw Pittman LLP

(57) ABSTRACT

Disclosed is a pericardiocentesis needle component (10), comprising a guide wire (13) and a puncture needle (12). The guide wire (13) extends into and through the puncture needle (12), and the guide wire (13) comprises a bent section (32) at the distal end and a straight section at the proximal end. The bent section (32) at the distal end is formed by bending the guide wire (13), and the end of the bent section is a pointed-shape structure. The guide wire (13) is made of a highly elastic material. The pointed end rotates at least 90 degrees within a range of no more than 3 mm starting from the pointed end at the bent section (32) of the guide wire. The pericardiocentesis needle component (10) of the present invention is less likely to damage a heart during a pericardiocentesis procedure.

20 Claims, 5 Drawing Sheets

(52) U.S. Cl.
CPC ........... *A61B 2017/00331* (2013.01); *A61B 2017/00867* (2013.01); *A61B 2017/22042* (2013.01); *A61B 2017/22044* (2013.01); *A61M 2025/09175* (2013.01)

(58) Field of Classification Search
CPC .......... A61B 2017/00247; A61B 2017/22044; A61B 2017/3405; A61M 2025/09175
USPC ........................................................ 606/185
See application file for complete search history.

(56) References Cited

U.S. PATENT DOCUMENTS

| | | | |
|---|---|---|---|
| 2005/0245876 A1 | 11/2005 | Khosravi et al. | |
| 2007/0005019 A1* | 1/2007 | Okishige | A61B 17/3478 604/175 |
| 2007/0021767 A1* | 1/2007 | Breznock | A61B 17/00234 606/185 |
| 2009/0105654 A1* | 4/2009 | Kurth | A61B 17/3468 604/170.03 |
| 2010/0114140 A1* | 5/2010 | Chanduszko | A61B 17/0057 606/185 |
| 2011/0087261 A1 | 4/2011 | Wittkampf et al. | |

FOREIGN PATENT DOCUMENTS

| | | |
|---|---|---|
| CN | 101066222 A | 11/2007 |
| CN | 201179264 Y | 1/2009 |
| CN | 101442946 A | 5/2009 |
| CN | 201404278 Y | 2/2010 |
| WO | WO 2009/112062 | 9/2009 |

* cited by examiner

PERICARDIOCENTESIS NEEDLE COMPONENT

CROSS REFERENCE TO RELATED APPLICATIONS

This application is the U.S. National Stage of PCT/CN2012/000728, filed May 25, 2012, which in turn claims the priority of Chinese application CN201110139534.9, filed on May 27, 2011, the entire contents of all applications are incorporated herein by reference in their entireties.

FIELD OF THE INVENTION

The present invention relates to a puncture needle assembly, and more particularly, it relates to a pericardium puncture needle assembly.

BACKGROUND OF THE INVENTION

Pericardium is a layer of connective tissue membrane that tightly wraps around the heart. In epicardial ablation, it is necessary to manually open a path through the pericardium tightly around the heart, in order to let the ablation catheter to access the space between the pericardium and the outwall of heart to conduct ablation.

There are a great diversity of pericardium puncture equipments on market. For example, Chinese patent CN00257117.X disclosed a type of noninvasive pericardium puncture needle, which comprises an outer sheath, an inner needle, and an end cap. The outer sheath is a flexible hollow tube that accommodates the inner needle. The inner needle is a solid puncture needle, which is fixed to the distal end of the outer sheath by the end cap. Once the pericardium is pierced by the needle, the needle is then withdrawn. The outer sheath continues advancing into the pericardium, so that the pericardial effusion can be extracted or drugs can be injected.

However, most of existing puncture needles are straight needle structure. In clinical operations, such a structure often pierces insufficiently and leads to puncture failure, or sometimes it tends to over-pierce and hurts the heart.

SUMMARY OF THE INVENTION

The present invention provides a pericardium puncture needle assembly, characterized in comprising a guide wire and a puncture needle, wherein the guide wire extends within the puncture needle, the guide wire has a curved distal section and a straight proximal section, the curved distal section is formed by bending the guide wire, the tip end of the curved distal section is a sharp tip structure, the guide wire is made from highly elastic material, the sharp tip bends at least 90 degrees within a length range of no more than 3 mm starting from the sharp tip of the curved distal section of the guide wire.

Preferably, the sharp tip bends at least 90 degrees within a length range of 1-2 mm starting from the sharp tip of the curved distal section of the guide wire.

Preferably, within a length range of no more than 3 mm starting from the sharp tip, the sharp tip structure comprises a curved section, which has a curvature radius of less than 2 mm.

After the sharp tip bends 90 degrees, a curved shape, starting from the proximal end of the sharp tip structure, of the curved distal section is involute curve, helix curve, or irregular curve.

In one exemplary embodiment, after the sharp tip bends 90 degrees, the curved shape, starting from the proximal end of the sharp tip structure, of the curved distal section is involute curve or helix curve with a curvature radius increasing gradually or stepwise.

In one exemplary embodiment, after the sharp tip bends 90 degrees, the curved shape, starting from the proximal end of the sharp tip structure, of the curved distal section is irregular curved shape including at least one curved section.

Preferably, the curved shape, starting from the proximal end of the sharp tip structure, of the curved distal section includes a first curved section and a second curved section.

The curvature radius of the first curved section is not greater than 1.5 mm, and the curvature radius of the second curved section is not greater than 2 mm.

In one preferable embodiment, a part of the curved distal end extending from the proximal end of the sharp tip structure to the proximal end of the guide wire is in cylindrical shape, which has a diameter of 0.2-1 mm.

In another preferable embodiment, a part of the curved distal section extending from the proximal end of the sharp tip structure to the proximal end of the guide wire is in flat sheet shape, which has a width of 0.2-1 mm.

In one preferable embodiment, the puncture needle is formed by connecting two tubes, one is the distal end tube and the other is the proximal end tube, the distal end tube has a length of 40-100 mm, and the proximal end tube has a length of 60-120 mm.

The diameter of distal end of the puncture needle is smaller than the diameter of its proximal end.

The inner diameter of the proximal end of the puncture needle is 0.5-2.5 mm, and the inner diameter of its distal end is 0.2-1.5 mm.

Preferably, an outer sheath is nested around the puncture needle, and the distal end of the outer sheath is in a spherical structure.

It is not likely to hurt the heart during pericardium puncture with the pericardium puncture needle assembly in preferable embodiments of the invention.

DETAILED DESCRIPTION OF THE INVENTION

This invention will now be described and explained in detail through embodiments and in combination with the drawings. However, this invention is not limited to the following embodiments.

Figure 1:
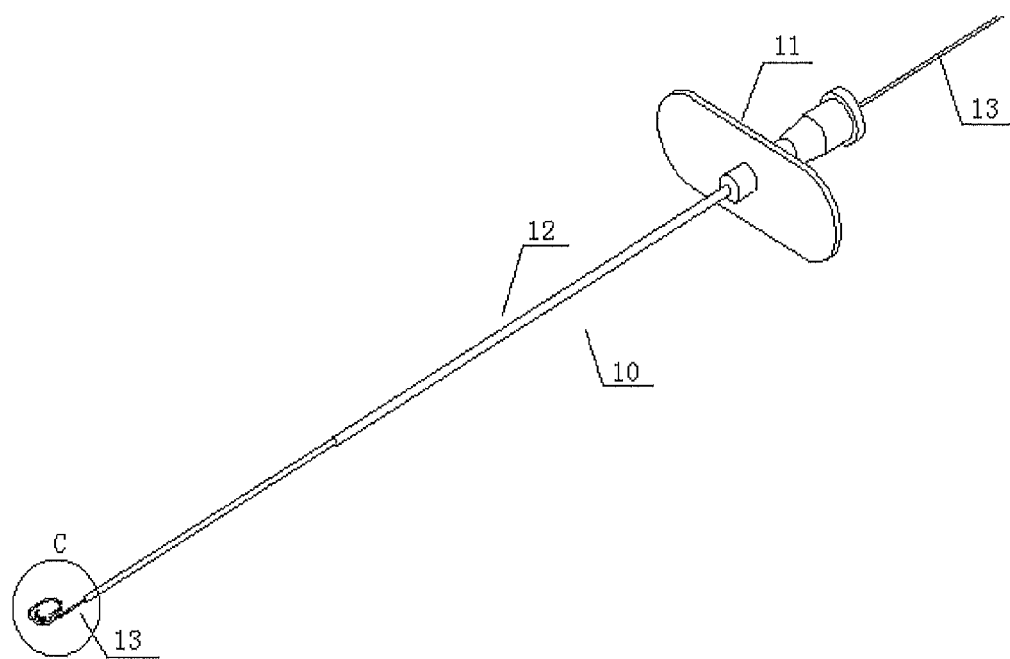
FIG. 1 is a structural perspective view of the pericardium puncture needle assembly according to one exemplary embodiment of the present invention.

FIG. 1 is a perspective view of the pericardium puncture needle assembly 10 according to one exemplary embodiment of the present invention, which comprises a needle 12 and a guide wire 13 extending within the needle 12. The guide wire 13 has an elongated, bendable flexible construction, which comprises a curved distal section and a straight proximal section. The curved distal section of guide wire 13 is formed by bending the guide wire, and its tip end is a sharp tip structure. The guide wire 13 is made from highly elastic material. The curved distal section is adapted to regain its preset curved shape from straightened state. The sharp tip, within a length range of no more than 3 mm starting from the sharp tip of the curved distal section of the guide wire, bends at least 90 degrees. Once the pericardium is pierced by the sharp tip of the guide wire, the angle between the pointing direction of the sharp tip and the advancing direction of guide wire is bigger than 90 degrees. Therefore, it is less likely to hurt the pericardium. The sharp tip structure of this invention means such a part of the guide wire that is within a length range of no more than 3 mm starting from the sharp tip and in which the sharp tip bends through 90 degrees. The curvature radius of the surface of the sharp tip is not greater than 0.1 mm. The sharp tip structure comprises a distal end and a proximal end. The sharp tip mentioned above means the distal end of the sharp tip structure, and the sharp tip is extremely sharp and may be a spherical structure at the micro level. A connector 11 is fixed at the proximal end of the puncture needle 12.

Figure 2:
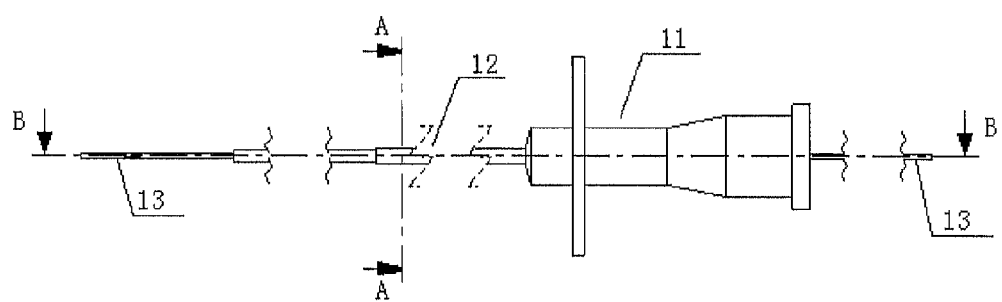
FIG. 2 is a plan view of the pericardium puncture needle assembly according to one exemplary embodiment of the present invention.
Figure 3:
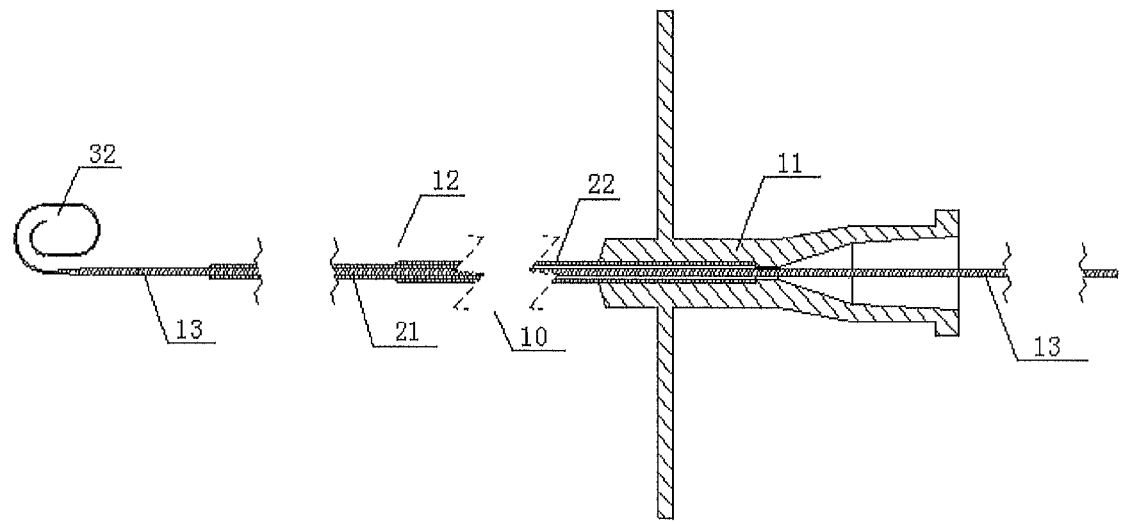
FIG. 3 is a sectional view taken along line B-B as shown in FIG. 2, which illustrates the inner structure of the pericardium puncture needle assembly according to one exemplary embodiment of the present invention.
Figure 4:
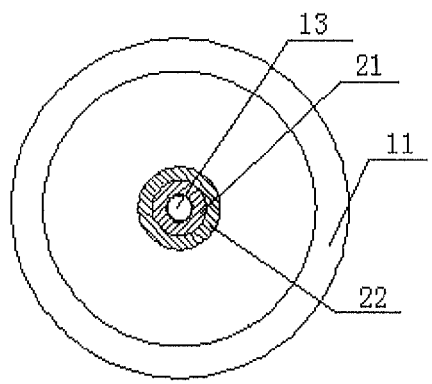
FIG. 4 is a sectional view taken along line A-A shown in FIG. 2, which illustrates the sectional structure of the pericardium puncture needle assembly according to one exemplary embodiment of the present invention.

FIG. 2 is a schematic plan view of the pericardium puncture needle assembly 10 according to one exemplary embodiment of the present invention; FIG. 3 is the sectional view of the pericardium puncture needle assembly 10 according to one exemplary embodiment of the present invention, which illustrates the connecting relationships of the connector 11, the puncture needle 12, and the guide wire 13; and FIG. 4 is the cross sectional view taken along line B-B indicated in FIG. 2. The puncture needle 12 has a tubular construction with a distal end and a proximal end, and may be made from any suitable biocompatible materials, such as stainless steel or nickel titanium alloy. The distal end of needle 12 may has a structure without or with a needlepoint.

The puncture needle 12 may be formed by a single tube, or can be joined by two sections of tubes. While the puncture needle 12 is joined by two sections of tubes, it may include a distal end tube 21 and a proximal end tube 22, as shown in FIG. 3. One means for connecting the distal end tube 21 and proximal end tube 22 is to insert one end of the distal end tube 21 into the proximal end tube 22, and fix them by bonding or welding. The distal end tube 21 and proximal end tube 22 may be made from the same materials, or different materials. For example, the distal end tube 21 is made from nickel titanium alloy, while the proximal end tube 22 is made from stainless steel, a matter which insures that the puncture needle 12 has a certain degree of curvature while in human body.

The diameter of puncture needle 12 may be set according to actual need of applications by those skilled in the art. The puncture needle 12 may has a tubular structure with a constant diameter, or with different diameters at the distal end and the proximal end. While the puncture needle 12 has a constant diameter, the diameter may be 0.5-1.0 mm. While the puncture needle 12 has different diameters at the distal end and proximal end, preferably, the diameter of the distal end is smaller than the diameter of proximal end, because the puncture needle 12 needs to provide some supporting force at the proximal end, while the distal end of the puncture needle 12 needs to be flexible in order to bend. In one exemplary embodiment of the present invention, the inner diameter of the proximal end of the puncture needle 12 is 0.5-2.5 mm, and the inner diameter of the distal end is 0.2-1.5 mm.

The length of the puncture needle 12 may be set according to actual need of applications by those skilled in the art. In one exemplary embodiment of the present invention, when the puncture needle 12 is made by connecting the distal end tube 21 and proximal end tube 22, the length of the distal end tube 21 may be 40-100 mm, and the length of the proximal end tube 22 may be 60-120 mm. The length of the connecting part may be set according to actual need of applications by those skilled in the art.

Figure 5:
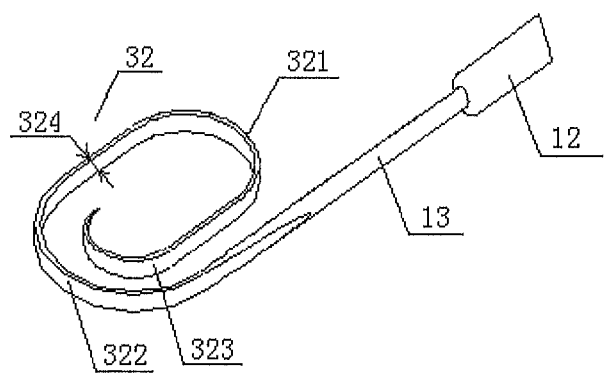
FIG. 5 is the enlarged view of part C of FIG. 1, which illustrates the structure of the curved distal section according to one exemplary embodiment of the present invention.
Figure 6:
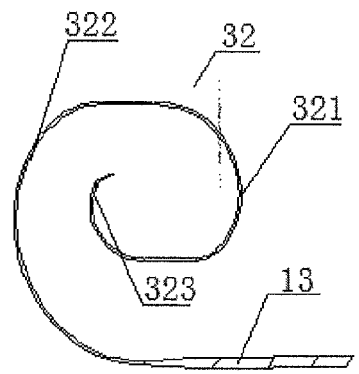
FIG. 6 illustrates the structure of the curved distal section of the guide wire 13 according to another exemplary embodiment of the present invention.

FIG. 5 shows an enlarged view of part C of FIG. 1, illustrating the structure of the curved distal section of the guide wire 13 of the pericardium puncture needle assembly according to one exemplary embodiment of the present invention, and FIG. 6 shows the structure of the curved distal section of the guide wire 13 of the pericardium puncture needle assembly according to another exemplary embodiment of the present invention. As shown in FIG. 3, FIG. 5, and FIG. 6, the guide wire 13 has an elongated and bendable flexible construction, which may be made from any suitable highly elastic materials, such as nickel titanium alloys. The guide wire 13 comprises a curved distal section 32 and a straight proximal section, and the curved distal section 32 is formed by bending the guide wire. The curved distal section 32 has such a structure that is adapted to regain its preset curved shape from straightened state. Because the guide wire is made from highly elastic material, the curved distal section 32 is in a straightened state when it is placed within the puncture needle 12, and regains its preset curved shape when it passes through the puncture needle 12. The curved distal section 32 and the guide wire 13 may be formed integrately, or formed separately. The guide wire 13 may be a solid structure without cavity inside, or may be any other suitable structures.

As shown in FIG. 3, FIG. 5, and FIG. 6, the tip end of the curved distal section 32 has a sharp tip structure, which is used for piercing pericardium without inducing any hurt. The sharp tip bends at least 90 degrees within a length range of no more than 3 mm starting from the sharp tip of the curved distal section of the guide wire. Preferably, the sharp tip bends at least 90 degrees within a length range of no more than 1-2 mm starting from the sharp tip of the curved distal section of the guide wire. Within a length range of no more than 3 mm starting from the sharp tip of the curved distal section of the guide wire, the sharp tip structure comprises a curved section 323 which has a curvature radius of no more than 2 mm.

As shown in FIG. 3, FIG. 5, and FIG. 6, after the sharp tip bends 90 degrees, the curved shape of the curved distal section 32 starting from the proximal end of the sharp tip structure may be helix curve, involute curve, or other suitable irregular curves, such as combination of arcs and straight line, combination of involute curve and straight line, or any other appropriate curved shapes. When the curved shape, starting from the proximal end of the sharp tip structure, of the curved distal section 32 is helix curve or involute curve, its curvature radius may increase gradually or stepwise. When the curved shape, starting from the proximal end of the sharp tip structure, of the curved distal section 32 is irregular curve, such as combination of arcs and straight line, combination of involute curve and straight line, or any other appropriate curved shapes, its curvature radius may change irregularly, e.g. increasing gradually or stepwise, but decreasing along with the further bending of the guide wire, and then increasing again gradually or stepwise. After the pericardium is pierced by the sharp tip of the curved distal section 32, the angle between the advancing direction of the guide wire and the pointing direction of the sharp tip is bigger than 90 degrees, thus avoiding piercing the heart. Even if the angle between the advancing direction of the guide wire and the pointing direction of the sharp tip is less than 90 degrees when the curved distal section 32 enters the pericardium gradually, it is not likely to hurt the heart, because the guide wire is very long and flexible, and thus the force of the guide wire is not able to be delivered to the sharp tip. Besides, the sharp tip may be encircled by the curved shape of the curved distal section, and is less likely to hurt the pericardium during piercing. Even if the sharp tip is not encircled by the curved shape of the curved distal section, the force of the guide wire is not able to be delivered to the sharp tip because the guide wire is very long and flexible. Therefore, it is not likely to hurt the heart.

As shown in FIG. 5, in this embodiment, after the sharp tip bends 90 degrees, the curved shape of the curved distal section 32 starting from the proximal end of the sharp tip structure is a combination of involute curve and straight line. As shown in FIG. 6, in this embodiment, after the sharp tip bends 90 degrees, the curved shape of the curved distal section 32 starting from the proximal end of the sharp tip structure is a combination of helix curve and straight line. The curved distal section 32 comprises at least one curved section, which may be one curved section, two curved sections, three curved sections or more curved sections. As shown in FIG. 5 and FIG. 6, the curved shape, starting from the proximal end of the sharp tip structure, of the curved distal section 32 includes a first curved section 321 and a second curved section 322. Preferably, the part of guide wire between the first curved section 321 and the second curved section 322, and the part of guide wire between the second curved section 322 and the curved section 323 of the sharp tip structure extend along a direction parallel to the puncture needle 12. The part of guide wire between the first curved section 321 and the second curved section 322, and the part of guide wire between the second curved section 322 and the curved section 323 of the sharp tip structure may be in the form of straight line.

The curvature radius of the first curved section 321 and the second curved section 322 may be set according to actual need of applications by those skilled in the art. For example, in one exemplary embodiment of the present invention, the curvature radius of the first curved section 321 is not greater than 1.5 mm, and the curvature radius of the second curved section 323 is not greater than 2 mm.

The part of the curved distal section 32 extending from the proximal end of the sharp tip structure to the proximal end of the guide wire may be cylindrical, the diameter of which may be set according to actual need of applications by those skilled in the art. For example, the diameter is 0.2-1 mm in one preferred embodiment of the present invention. The part of the curved distal section 32 extending from the proximal end of the sharp tip structure to the proximal end of the guide wire may also be a flat sheet shape, which has a width of 0.2-1 mm as shown in FIG. 5. The width of the flat sheet shape structure means the width indicated by symbol 324 in FIG. 5.

A sheath, not shown in figures, may be disposed within the puncture needle 12 as shown in FIG. 1, FIG. 2, and FIG. 3. The sheath extends within the puncture needle 12. The proximal end of the sheath is fixed to the connector 11. The distal end of the sheath may be a free end, or may also be fixed to the distal end of the puncture needle 12. The distal end of the guide wire 13 enters the puncture needle 12 through the sheath, and extends within the puncture needle 12 along its axial direction. The proximal end of guide wire 13 may be fixed to the connector 11 depending on actual needs, or may be a free end without being fixed. It is possible that there is no sheath within the puncture needle 12. The guide wire 13 is pushed through the puncture needle 12 by a guide wire pusher when the puncture needle is used. The guide wire pusher also works as a sheath.

The connector 11, which is fixed to the proximal end of the puncture needle 12, may be a luer connector. Once completing piercing and drawing out the guide wire 13, the connector may be used for injecting drugs or other liquids, or extracting effusion from the body.

According to one preferable embodiment of the present invention, during the use of pericardium puncture needle assembly, the curved distal section 32 is in straightened state while it is wholly within the puncture needle 12. When pushing forward the guide wire 13, the sharp tip of the curved distal section 32 pierces the pericardium, and the guide wire 13 gradually enters the pericardium. The curved distal section 32 gradually becomes curved until regaining its preset shape. The puncture needle 12 enters into the pericardium, and the piercing procedure is finished. Then the guide wire 13 is drawn out of human body. During the drawing out of the guide wire 13, it gradually regains straightened state from curved state, and is withdrawn into the puncture needle 12. After the guide wire 13 is drawn out of the body, it is possible to inject drugs or contrast agents, or extract pericardial effusion through the connector 11.

Figure 7:
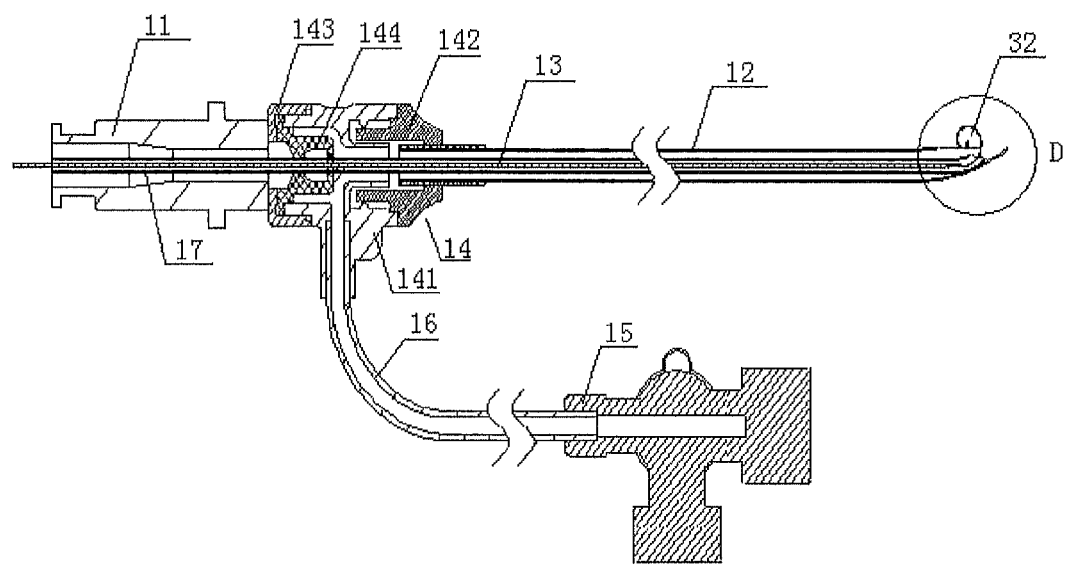
FIG. 7 is a structural perspective view of the pericardium puncture needle assembly 10 according to another exemplary embodiment of the present invention.
Figure 8:
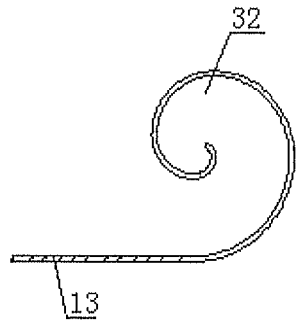
FIG. 8 is the enlarged view of the part D of FIG. 7.

FIG. 7 is a perspective structural view of the pericardium puncture needle assembly 10 according to another exemplary embodiment of the present invention. FIG. 8 is the enlarged view of the part indicated by symbol D of FIG. 7. As shown in FIG. 7 and FIG. 8, the pericardium puncture needle assembly 10 comprises puncture needle 12, and the guide wire 13 extends within the needle 12. The guide wire 13 is a bendable, elongated flexible construction including a distal end and a proximal end. The guide wire 13 includes a curved distal section 32 and a straight proximal section. The curved distal section comprises a sharp tip structure at its distal end. A negative pressure device is fixed to the proximal end of the puncture needle 12. The distal end of the puncture needle comprises a lateral abutment area in order to form certain suction area between the distal end of the puncture needle and the pericardial tissue, thus producing negative pressure.

The guide wire 13 is made from highly elastic material. The curved distal section 32 is formed by bending the guide wire, and has such a structure that is adapted to regain its preset curved shape from straightened state. The sharp tip bends at least 90 degrees within a length range of no more than 3 mm starting from the sharp tip of the curved distal section of the guide wire. The curved distal section 32 may be in any other suitable curved shape. Within a length range of no more than 3 mm starting from the sharp tip, the sharp tip structure comprises a curved section with a curvature radius of not greater than 2 mm. When the sharp tip bends 90 degrees, the curved distal section 32, starting from the proximal end of the sharp tip structure, may be involute curve, e.g. square involute, triangle involute, or any other involutes, the curvature radius of which increases continuously or stepwise, as shown in FIG. 7 and FIG. 8.

The negative pressure device comprises a junction valve 14 and a negative pressure tee valve 15. The junction valve 14 and negative pressure tee valve 15 are connected by a negative pressure tube 16. The junction valve 14 may be formed integrately, or formed in separate parts. As shown in FIG. 7, the junction valve 14 comprises a valve body 141. The valve body 141 includes a distal end, a proximal end and a central cavity. A lower end cap 142 is disposed at the distal end of the valve body 141, and an upper end cover 143 is disposed at the proximal end of the valve body 141. The proximal end of the puncture needle 12 is fixed inside the lower end cap 142, and a protective sheath may be disposed at the proximal end. A gasket 144 is disposed within the upper end cap 143 for sealing purpose. One end of the negative pressure connecting tube 16 is fixed to the junction valve 14, and the other end is fixed to the negative pressure tee valve 15.

Preferably, a sheath 17 is disposed within the puncture needle 12. The sheath 17 extends within the puncture needle 12, and the proximal end of sheath 17 extends out of the junction valve 14. The guide wire 13 extends through the sheath 17 into the puncture needle 12, and extends within the puncture needle 12.

A connector 11 is disposed at the proximal end of the junction valve 14, which may be a luer connector. After finishing piercing and drawing out the guide wire 13, the connector may be used for injecting drugs or other liquids into the body, or extracting pericardial effusion from the body.

In the embodiment shown in FIG. 7 and FIG. 8, the other structures of the guide wire 13 and puncture needle 12 are identical to those in the embodiments illustrated in FIG. 1 to FIG. 5.

Figure 9:
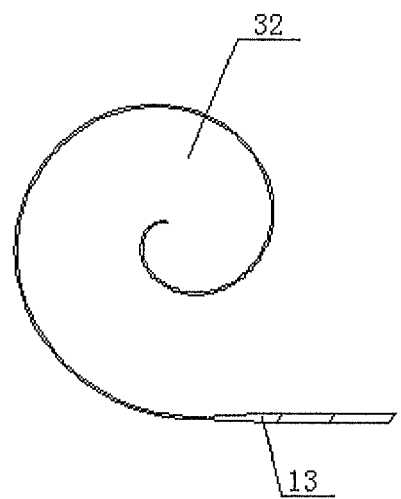
FIG. 9 is a structural perspective view of the curved distal section 32 according to another exemplary embodiment of the present invention.

FIG. 9 is a structural perspective view of the curved distal section 32 according to another embodiment of the present invention. As shown in FIG. 9, the guide wire 13 is an elongated and bendable flexible structure, which includes a curved distal section 32 and a straight proximal section. The guide wire is made from highly elastic material. The curved distal section 32 is formed by bending the guide wire 13, and comprises a sharp tip structure at its distal end. The curved distal section 32 has such a structure that is adapted to regain its preset curved shape from straightened state.

The sharp tip bends at least 90 degrees within a length range of no more than 3 mm starting from the sharp tip of the curved distal section of the guide wire. Within a length range of no more than 3 mm starting from the sharp tip, the sharp tip structure comprises a curved section, which has a curvature radius of not greater than 2 mm. After the sharp tip bends 90 degrees, the curved shape of the curved distal section of the guide wire starting from the proximal end of the sharp tip structure may be helix curve, which has a curvature radius increasing continuously, as shown in FIG. 9. The curved distal section 32 may be in form of other suitable curved shape.

Figure 10:
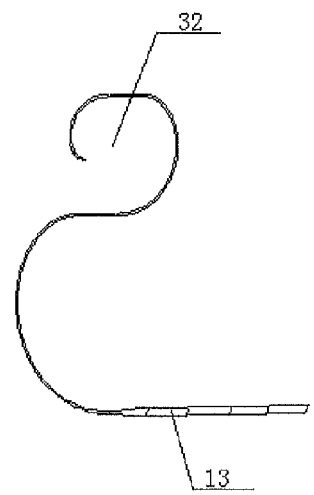
FIG. 10 is a structural perspective view of the curved distal section 32 according to another exemplary embodiment of the present invention.

FIG. 10 is a structural perspective view of the curved distal section 32 according to another embodiment of the present invention. As shown in FIG. 10, the guide wire 13 is an elongated and bendable flexible structure, which includes a curved distal section 32 and a straight proximal section. The guide wire is made from highly elastic material. The curved distal section 32 is formed by bending the guide wire 13, and includes a sharp tip structure at its distal end. The curved distal section 32 is such a structure that it is adapted to regain its preset shape from straightened state.

The sharp tip bends at least 90 degrees within a length range of no more than 3 mm starting from the sharp tip of the distal end of the guide wire. Within a length range of no more than 3 mm starting from the sharp tip, the sharp tip structure comprises a curved section, which has a curvature radius of not greater than 2 mm. After the sharp tip bends 90 degrees, the curved distal section 32, starting from the proximal end of the sharp tip structure, may be irregular curve, which has a curvature radius changing irregularly, as shown in FIG. 10. For example, the curvature radius may increase gradually or stepwise, but decrease along with the further bending of the guide wire, and then increase again gradually or stepwise, or it may repeatedly change as above. The curved distal section 32 may be in form of other suitable curved shape.

Figure 11:
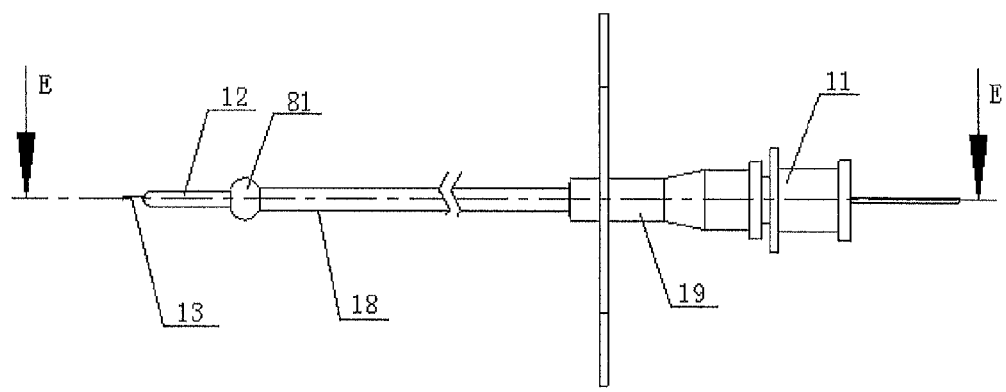
FIG. 11 is a structural perspective view of the pericardium puncture needle assembly 10 according to another exemplary embodiment of the present invention.
Figure 12:
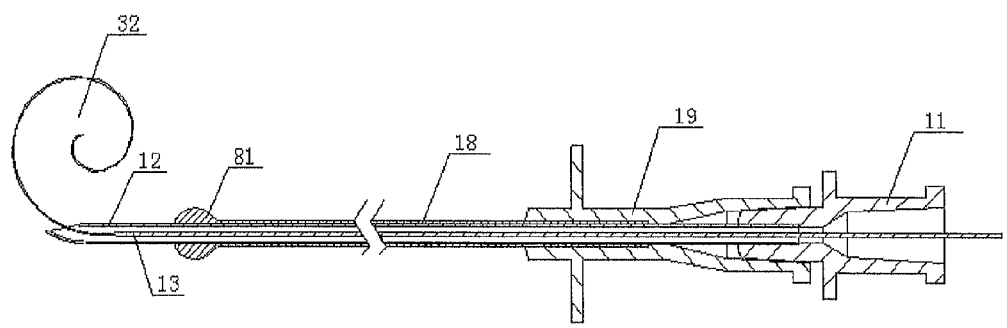
FIG. 12 is a sectional view taken along line E-E of FIG. 11.

FIG. 11 is a structural perspective view of the pericardium puncture needle assembly 10 according to another preferable embodiment of the present invention. FIG. 12 is the cross sectional view taken as indicated by arrows E-E of FIG. 11. As shown in FIG. 11 and FIG. 12, the pericardium puncture needle assembly 10 comprises a puncture needle 12, and a guide wire 13 extends within the puncture needle 12. The guide wire 13 is an elongated and bendable flexible structure, which includes a curved distal section 32 and a straight proximal section. The guide wire is made from highly elastic material. The curved distal section 32 is formed by bending the guide wire 13, which includes a sharp tip structure at its distal end. The curved distal section 32 is adapted to regain its preset curved shape from straightened state. The sharp tip bends at least 90 degrees within a length range of no more than 3 mm starting from the sharp tip of the distal end of the guide wire. Within a length range of no more than 3 mm starting from the sharp tip, the sharp tip structure comprises a curved section, which has a curvature radius of not greater than 2 mm. A connector 11 is fixed to the proximal end of the puncture needle 12.

After the sharp tip bends 90 degrees, the curved distal section 32, starting from the proximal end of the sharp tip structure, may be helix curve, which has a curvature radius increasing continuously, as shown in FIG. 11 and FIG. 12. The curved distal section 32 may be in form of other suitable curved shape.

An outer sheath 18, which comprises a distal end and a proximal end, is nested outside the puncture needle 12. The distal end of the outer sheath 18 is a spherical structure 81, or may be other suitable shape. The spherical structure 81 and the outer sheath 18 may be formed separately or integrately. The outer sheath 18 may be made from any suitable biocompatible materials, e.g. stainless steel. When the spherical structure 81 is formed separately to the outer sheath 18, they may be made from the same material, or from different materials. The proximal end of the outer sheath 18 is fixed to a connector 19 by bonding or other suitable methods. The connector 19 may be any suitable configuration, e.g. luer connector. The connector 11 may slide freely at the proximal end of the connector 19, or be fixed through self-locking. After entering into thoracic cavity, the distal end of the puncture needle 12 may be withdrawn into the outer sheath 18 by controlling the connector 11. Therefore, while the outer sheath 18 is pushed forward, it is less likely to hurt the tissue. During the pericardium puncture procedure, the distal end of the puncture needle 12 may be used to abut on the pericardium, or alternatively, the puncture needle 12 may be withdrawn and the spherical structure 81 of the distal end of the outer sheath may be directly used to abut on the pericardium, so as to complete the punctured procedure.

The embodiments of present invention are not limited to those embodiments described above. Without departing from the spirit and scopes of the present invention, various variations and improvements may be made to the invention in forms and details by those skilled in the art, all of which are regarded as falling into the protection scopes of the present invention.

The invention claimed is:

1. A pericardium puncture needle assembly, the assembly comprising a guide wire and a puncture needle, wherein the guide wire extends within the puncture needle, the puncture needle extending along a longitudinal axis, the guide wire has a distal section and a straight proximal section, the distal section is formed by bending the guide wire and has a preset curved shape, the tip end of the distal section is a sharp tip structure, the distal section of the guide wire is configured to adopt a straightened state within the puncture needle and is configured to regain the preset curved shape when it passes out of the puncture needle, the sharp tip bends at least 90 degrees within a length range of no more than 3 mm starting from the sharp tip of the distal section of the guide wire in the preset curved shape, and the sharp tip is encircled by the preset curved shape of the distal section, and wherein the longitudinal axis of the puncture needle, the preset curved shape of the distal section, and the sharp tip all are within the same plane.

2. The pericardium puncture needle assembly of claim 1, characterized in that the length range of the sharp tip is 1-2 mm.

3. The pericardium puncture needle assembly of claim 2, characterized in that after the sharp tip bends 90 degrees, a curved shape, starting from the proximal end of the sharp tip structure, of the distal section in the preset curved shape is involute curve, helix curve, or irregular curve.

4. The pericardium puncture needle assembly of claim 3, characterized in that after the sharp tip bends 90 degrees, the curved shape, starting from the proximal end of the sharp tip structure, of the distal section in the preset curved shape is involute curve or helix curve with a curvature radius increasing gradually or stepwise toward the proximal end of the guide wire.

5. The pericardium puncture needle assembly of claim 3, characterized in that a part of the distal section extending from the proximal end of the sharp tip structure to the proximal end of the guide wire is in flat sheet shape, which has a width of 0.2-1 mm.

6. The pericardium puncture needle assembly of claim 2, characterized in that a part of the distal section extending from the proximal end of the sharp tip structure to the proximal end of the guide wire is in flat sheet shape, which has a width of 0.2-1 mm.

7. The pericardium puncture needle assembly of claim 2, characterized in that the distal end of the puncture needle has a structure without a needlepoint.

8. The pericardium puncture needle assembly of claim 1, characterized in that within the length range, the sharp tip structure comprises a curved section, which has a curvature radius of less than 2 mm.

9. The pericardium puncture needle assembly of claim 1, characterized in that after the sharp tip bends 90 degrees, a curved shape, starting from the proximal end of the sharp tip structure, of the distal section in the preset curved shape is involute curve, helix curve, or irregular curve.

10. The pericardium puncture needle assembly of claim 9, characterized in that after the sharp tip bends 90 degrees, the curved shape, starting from the proximal end of the sharp tip structure, of the distal section in the preset curved shape is involute curve or helix curve with a curvature radius increasing gradually or stepwise toward the proximal end of the guide wire.

11. The pericardium puncture needle assembly of claim 9, characterized in that after the sharp tip bends 90 degrees, the curved shape, starting from the proximal end of the sharp tip structure, of the distal section in the preset curved shape is irregular curved shape including at least one curved section.

12. The pericardium puncture needle assembly of claim 11, characterized in that the curved shape, starting from the proximal end of the sharp tip structure, of the distal section in the preset curved shape includes a first curved section and a second curved section.

13. The pericardium puncture needle assembly of claim 12, characterized in that a curvature radius of the first curved section is not greater than 1.5 mm, and a curvature radius of the second curved section is not greater than 2 mm.

14. The pericardium puncture needle assembly of claim 1, characterized in that a part of the distal section extending from the proximal end of the sharp tip structure to the proximal end of the guide wire is in cylindrical shape, which has a diameter of 0.2-1 mm.

15. The pericardium puncture needle assembly of claim 1, characterized in that a part of the distal section extending from the proximal end of the sharp tip structure to the proximal end of the guide wire is in flat sheet shape, which has a width of 0.2-1 mm.

16. The pericardium puncture needle assembly of claim 1, characterized in that the puncture needle is formed by connecting two tubes, one is a distal end tube and the other is a proximal end tube, the diameter of the distal end of the puncture needle is smaller than the diameter of its proximal end, the inner diameter of the proximal end of the puncture needle is 0.5-2.5 mm, and the inner diameter of its distal end is 0.2-1.5 mm.

17. The pericardium puncture needle assembly of claim 1, characterized in that a negative pressure device is fixed at the proximal end of the puncture needle.

18. The pericardium puncture needle assembly of claim 1, characterized in that an outer sheath is nested outside the puncture needle, and the distal end of the outer sheath is in a spherical structure.

19. The pericardium puncture needle assembly of claim 1, characterized in that the distal end of the puncture needle has a structure without a needlepoint.

20. The pericardium puncture needle assembly of claim 1, characterized in that a sheath is disposed inside the puncture needle, and the guide wire extends within the sheath.

* * * * *